US00PP21976P2

(12) United States Plant Patent
Wood

(10) Patent No.: US PP21,976 P2
(45) Date of Patent: Jun. 14, 2011

(54) ***SPIRAEA* PLANT NAMED 'ZELDA'**

(50) Latin Name: ***Spiraea fritschiana*×*Spiraea japonica***
Varietal Denomination: Zelda

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/653,753

(22) Filed: Dec. 16, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP15,397 P2 * 12/2004 Wood ..... Plt./226
2002/0169076 A1 11/2002 Takeshi et al.
2004/0058149 A1 3/2004 Zhou et al.
2007/0184975 A1 8/2007 Yi et al.

OTHER PUBLICATIONS

UPOV GTITM ROM Computer Database GTI Jouve Retrieval Software 2010/03 Citation for 'Zelda'.*
Jing Li et al. Journal of the Electrochemical Society. 2007, vol. 154. No. 11, pp. C631 to C636.
Kuo-Pin Yu et al . Applied Catalysis B: Environmental. 2008 , vol. 84, pp. 112 to 118.
Jiaqing Geng et al. Materials Research Bulletin. 2009, vol. 44, pp. 146 to 150.

* cited by examiner

*Primary Examiner* — Wendy Haas
(74) *Attorney, Agent, or Firm* — C. A. Whealy

(57) ABSTRACT

A new and distinct cultivar of *Spiraea* plant named 'Zelda', characterized by its compact, upright, outwardly spreading and mounding plant habit; vigorous growth habit; freely branching habit; developing leaves that are orange red in color and become yellow green in color with development; numerous dark pink-colored flowers; and good garden performance.

3 Drawing Sheets

Botanical designation: *Spiraea fritschiana*×*Spiraea japonica.*
Cultivar denomination: 'ZELDA'.

BACKGROUND OF THE INVENTION

The present invention relates to a new and distinct cultivar of *Spiraea* plant, botanically known as *Spiraea fritschiana*× *Spiraea japonica* and hereinafter referred to by the name 'Zelda'.

The new *Spiraea* plant is a product of a planned breeding program conducted by the Inventor in Grand Haven, Mich. The objective of the breeding program is to develop new compact and mounding *Spiraea* cultivars with attractive foliage and flowers.

The new *Spiraea* plant originated from an open-pollination in 2003 of *Spiraea fritschiana* 'Wilma', disclosed in U.S. Plant Pat. No. 15,397, as the female, or seed, parent with an unknown selection of *Spiraea japonica,* as the male, or pollen, parent. The new *Spiraea* plant was discovered and selected by the Inventor in 2005 as a single flowering plant within the progeny of the stated open-pollination in a controlled environment in Grand Haven, Mich.

Asexual reproduction of the new *Spiraea* plant by softwood cuttings in a controlled greenhouse environment in Grand Haven, Mich. since the summer of 2005 has shown that the unique features of this new *Spiraea* plant are stable and reproduced true to type in successive generations of asexual reproduction.

SUMMARY OF THE INVENTION

Plants of the new *Spiraea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zelda'. These characteristics in combination distinguish 'Zelda' as a new and distinct cultivar of *Spiraea:*

1. Compact, upright, outwardly spreading and mounding plant habit.
2. Vigorous growth habit.
3. Freely branching habit.
4. Developing leaves that are orange red in color and become yellow green in color with development.
5. Numerous dark pink-colored flowers.
6. Good garden performance.

Plants of the new *Spiraea* can be compared to plants of the female parent, 'Wilma'. Plants of the new *Spiraea* differ from plants of 'Wilma' in the following characteristics:

1. Plants of the new *Spiraea* and 'Wilma' differ in leaf color as plants of 'Wilma' have green-colored developing and fully expanded leaves.
2. Plants of the new *Spiraea* have darker pink-colored flowers than plants of 'Wilma'.

Plants of the new *Spiraea* can be compared to plants of an unnamed selection of *Spiraea japonica*. Plants of the new *Spiraea* differ from plants of the unnamed selection in the following characteristics:

1. Plants of the new *Spiraea* are larger than plants of the unnamed selection.

2. Plants of the new *Spiraea* and the unnamed selection differ in developing leaf color as plants of the unnamed selection have red-colored developing leaves.
3. Plants of the new *Spiraea* have larger flowers than plants of the unnamed selection.

Plants of the new *Spiraea* can be compared to plants of the *Spiraea japonica* 'Gold Flame', not patented. Plants of the new *Spiraea* differ from plants of 'Gold Flame' in the following characteristics:

1. Plants of the new *Spiraea* are not as compact as plants of 'Gold Flame'.
2. Plants of the new *Spiraea* and 'Gold Flame' differ in developing leaf color and plants of 'Gold Flame' have red-colored developing leaves.
3. Plants of the new *Spiraea* have larger flowers than plants of 'Gold Flame'.
4. Plants of the new *Spiraea* and 'Gold Flame' differ in flower color as plants of 'Gold Flame' have darker pink-colored flowers.

BRIEF DESCRIPTION OF THE PHOTOGRAPHS

The accompanying colored photographs illustrate the overall appearance of the new *Spiraea* plant, showing the colors as true as it is reasonably possible to obtain in colored reproductions of this type. Colors in the photographs may differ slightly from the color values cited in the detailed botanical description which accurately describe the colors of the new *Spiraea* plant.

The photograph on the first sheet is a side perspective view of a typical plant of 'Zelda' grown in a container.

The photograph on the second sheet is a close-up view of typical developing and fully expanded leaves of 'Zelda'.

The photograph on the third sheet is a close-up view of a typical inflorescence and leaves of 'Zelda'.

DETAILED BOTANICAL DESCRIPTION

The aforementioned photographs and following observations, measurements and values describe plants of the new *Spiraea* grown in three-gallon containers in an outdoor nursery in Grand Haven, Mich. during the spring and summer under conditions which closely approximate commercial production. Plants were three years old when the photographs and the description were taken. In the description, color references are made to The Royal Horticultural Society Colour Chart, 1995 Edition, except where general terms of ordinary dictionary significance are used.

Botanical classification: *Spiraea fritschiana*×*Spiraea japonica* 'Zelda'.

Parentage:

*Female, or seed, parent.*—*Spiraea fritschiana* 'Wilma', disclosed in U.S. Plant Pat. No. 15,397.

*Male, or pollen, parent.*—Unknown selection of *Spiraea japonica*, not patented.

Propagation:

*Type.*—By softwood cuttings.

*Time to initiate roots.*—About 20 days at 25° C.

*Time to produce a rooted young plant.*—About three months at 25° C.

*Root description.*—Fine to thick, fibrous.

*Rooting habit.*—Freely branching; dense.

Plant description:

*Plant form and growth habit.*—Perennial shrub; compact, upright, outwardly spreading and mounding plant habit; vigorous growth habit.

*Branching habit.*—Freely branching habit with about 82 primary lateral branches; pinching (removal of terminal apices) will enhance lateral branch development.

*Plant height.*—About 65 cm.

*Plant diameter* (*area of spread*).—About 70 cm.

Lateral branch description:

*Length.*—About 25 cm.

*Diameter.*—About 1.5 mm.

*Internode length.*—About 2 cm.

*Texture.*—Smooth, glabrous.

*Color, developing.*—Close to 176A.

*Color, developed.*—Close to 145A.

Foliage description:

*Arrangement.*—Alternate, simple.

*Length.*—About 5 cm.

*Width.*—About 3 cm.

*Shape.*—Ovate to elliptical.

*Apex.*—Acute.

*Base.*—Cuneate.

*Margin.*—Serrulate to doubly serrate.

*Texture, upper and lower surfaces.*—Slightly pubescent.

*Venation pattern.*—Pinnate.

*Color.*—Developing leaves, upper surface: Close to 179B. Developing leaves, lower surface: Close to 179B to 179C. Fully expanded leaves, upper surface: Close to 153C; venation, close to 177B. Fully expanded leaves, lower surface: Close to 146D; venation, close to 181A.

*Petiole.*—Length: About 4 mm. Diameter: About 1 mm. Texture, upper and lower surfaces: Smooth, glabrous. Color, upper and lower surfaces: Close to 146C.

Flower description:

*Flower appearance/arrangement.*—Single rotate flowers arranged in compound corymbs; freely flowering habit with usually about 200 flowers per inflorescence; flowers face upright to outwardly.

*Natural flowering season.*—Continuous flowering from late spring through the summer in Grand Haven, Mich.

*Flower longevity.*—Flowers last about three to four weeks on the plant; flowers persistent.

*Fragrance.*—None detected.

*Inflorescence height.*—About 3.5 cm.

*Inflorescence diameter.*—About 7.5 cm.

*Flower diameter.*—About 4.5 mm.

*Flower length* (*height*).—About 5 mm.

*Flower bud.*—Length: About 2 mm. Diameter: About 3 mm. Shape: Globose. Color: Close to 66A.

*Petals.*—Quantity per flower: Single whorl of five. Length: About 2 mm. Width: About 2 mm. Shape: Oblong. Apex: Obtuse. Margin: Entire. Texture, upper and lower surfaces: Smooth, glabrous; silky. Color: When opening, upper and lower surfaces: Close to 66C. Fully opened, upper and lower surfaces: Close to 66D.

*Sepals.*—Quantity per flower: Single whorl of five. Length: About 1 mm. Width: About 1 mm. Shape: Subulate. Apex: Acute. Base: Fused. Margin: Entire. Texture, upper and lower surfaces: Smooth, glabrous. Color: When opening, upper surface: Close to 186A. When opening, lower surface: Close to 55A. Fully opened, upper surface: Close to 145A. Fully opened, lower surface: Close to 54A.

*Peduncles.*—Length: About 1.3 cm. Diameter: About 2 mm. Strength: Strong. Aspect: Erect to about 20° from vertical. Texture: Smooth, glabrous. Color: Close to 146D.

*Pedicels.*—Length: About 3 mm. Diameter: About 1 mm. Strength: Strong. Aspect: About 30° to 45° from peduncle axis. Texture: Smooth, glabrous. Color: Close to 146D.

*Reproductive organs.*—Androecium: Quantity per flower: About 18. Anther shape: Globose. Anther length: About 0.25 mm. Anther color: Close to 64A. Amount of pollen: Scarce. Pollen color: Close to 8D. Gynoecium: Quantity per flower: One. Pistil length: About 1 mm. Style length: About 0.75 mm. Style color: Close to 60B. Stigma appearance: Globose. Stigma color: Close to 60B. Ovary color: Close to 182C.

*Seeds.*—Length: About 1 mm. Diameter: About 0.5 mm. Color: Close to 161C.

Garden performance: Plants of the new *Spiraea* have been observed to have good garden performance and to tolerate rain, wind and temperatures ranging from about −29° C. to about 37° C.

Pathogen/pest resistance: Plants of the new *Spiraea* have not been observed to be resistant to pathogens and pests common to *Spiraea*.

It is claimed:

1. A new and distinct *Spiraea* plant named 'Zelda' as illustrated and described.

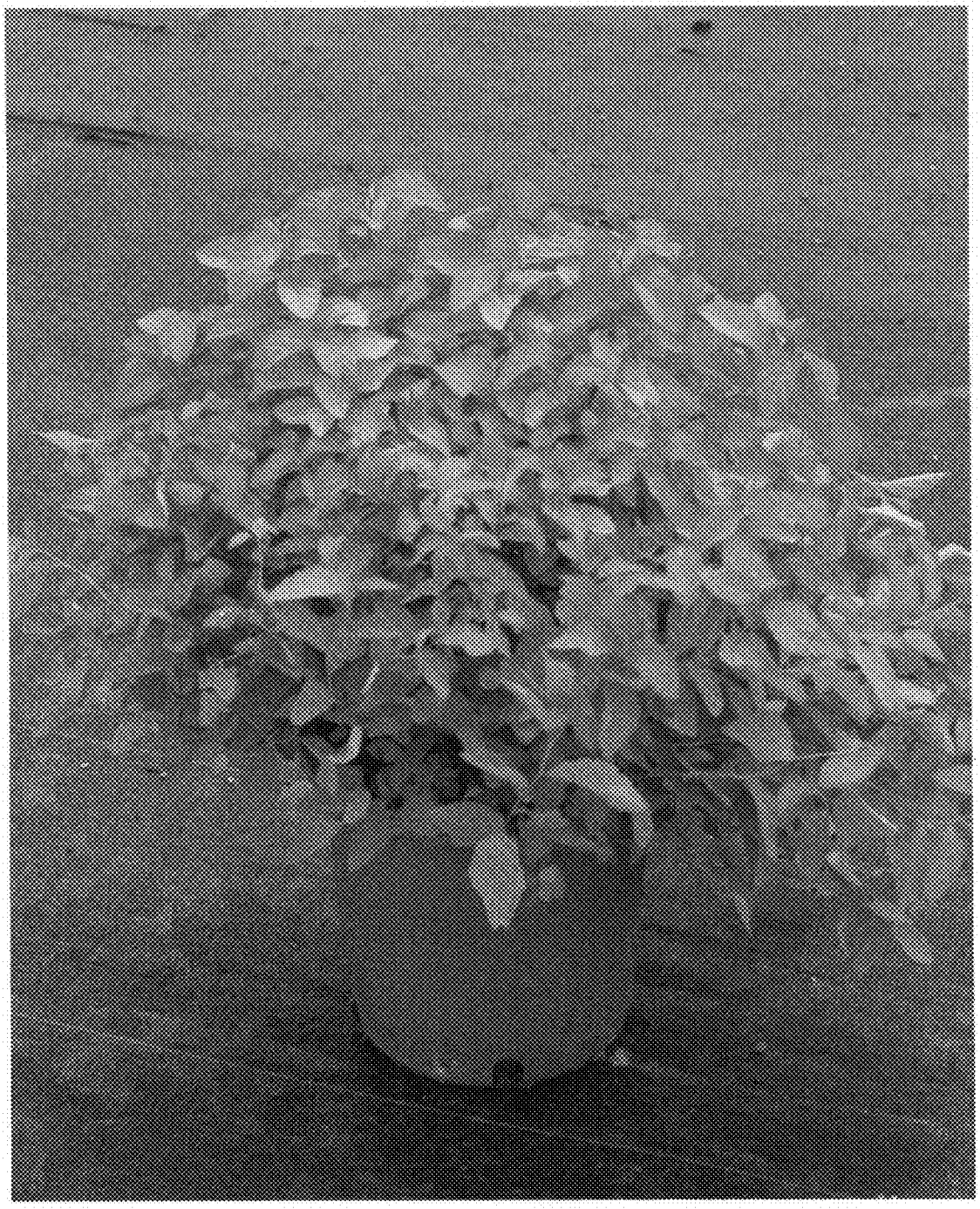

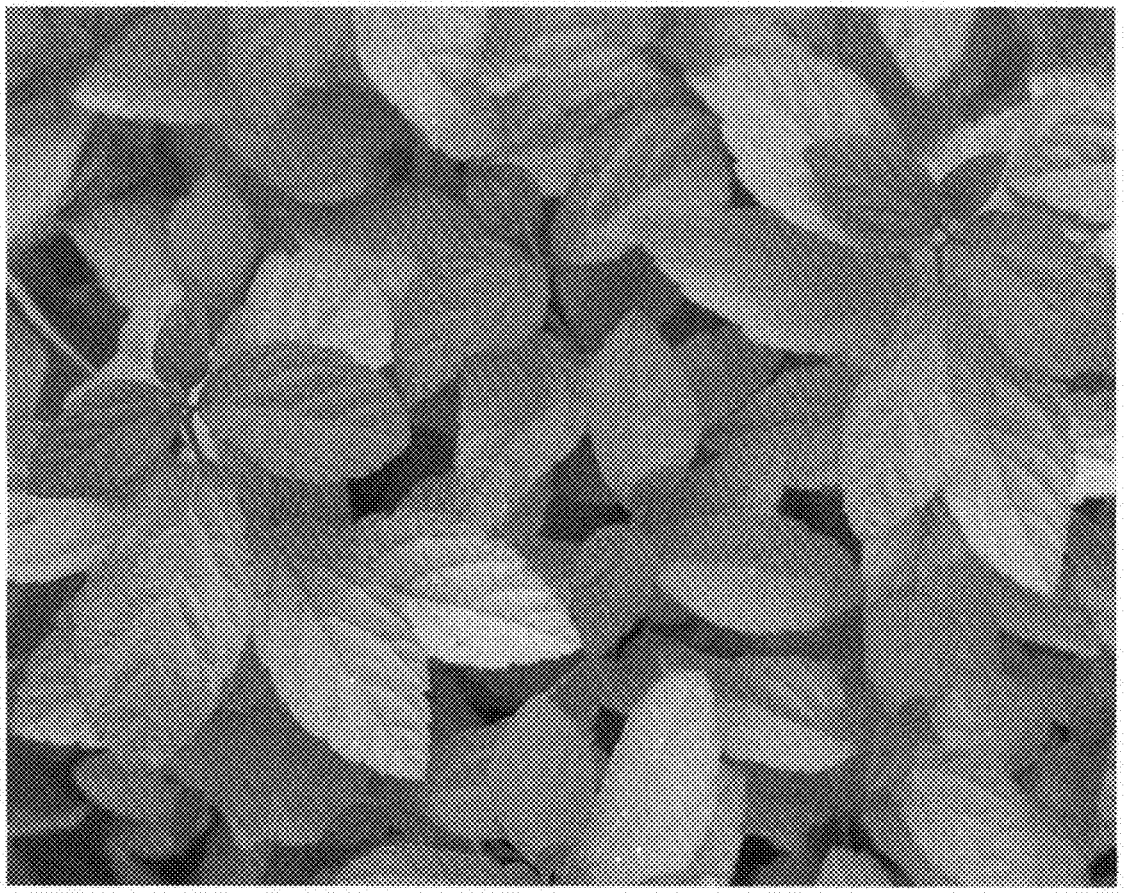

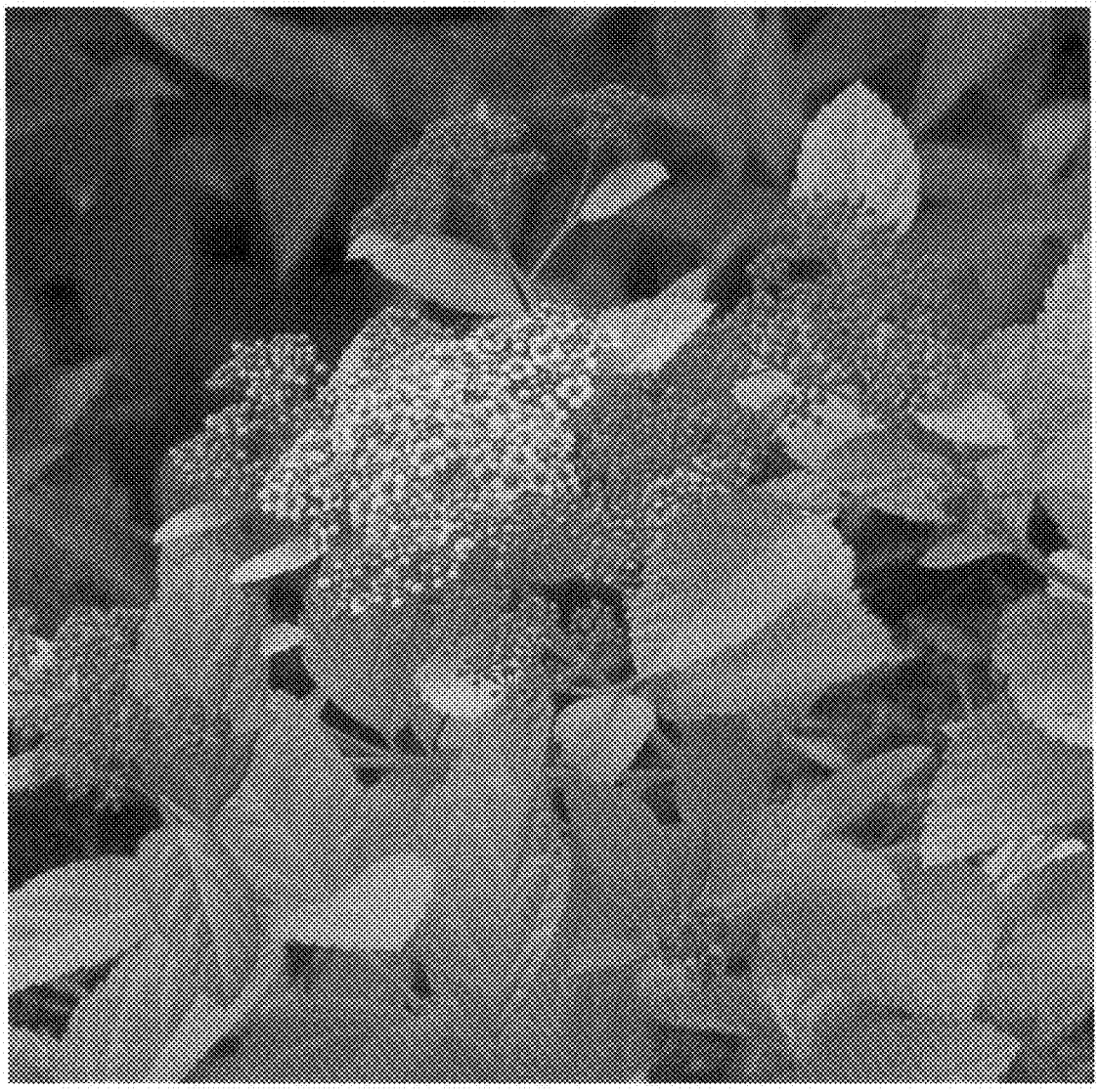

* * * * *